(12) United States Patent
Miyazaki

(10) Patent No.: US 8,205,616 B2
(45) Date of Patent: Jun. 26, 2012

(54) ANTENNA HOLDER FOR NAVIGATION SURGERY

(76) Inventor: Hidemi Miyazaki, Tokyo (JP)

( * ) Notice: Subject to any disclaimer, the term of this patent is extended or adjusted under 35 U.S.C. 154(b) by 0 days.

(21) Appl. No.: 13/063,562

(22) PCT Filed: Sep. 10, 2009

(86) PCT No.: PCT/JP2009/065802
§ 371 (c)(1),
(2), (4) Date: Mar. 11, 2011

(87) PCT Pub. No.: WO2010/029962
PCT Pub. Date: Mar. 18, 2010

(65) Prior Publication Data
US 2011/0174314 A1 Jul. 21, 2011

(30) Foreign Application Priority Data
Sep. 13, 2008 (JP) ................... 2008-235790

(51) Int. Cl.
*A61G 15/00* (2006.01)
*A61C 17/06* (2006.01)
*A61B 19/00* (2006.01)

(52) U.S. Cl. ............... 128/845; 433/93; 606/130

(58) Field of Classification Search .............. 600/426, 600/407; 606/130; 433/33, 25, 91, 93, 68; 128/845, 861, 859, 857, 46
See application file for complete search history.

(56) References Cited

U.S. PATENT DOCUMENTS

| | | | |
|---|---|---|---|
| 6,096,048 A | 8/2000 | Howard, III et al. | |
| 6,236,875 B1 | 5/2001 | Bucholz et al. | |
| 6,893,447 B2 | 5/2005 | Dominguez et al. | |
| 2003/0138755 A1* | 7/2003 | Tremont | 433/68 |
| 2004/0166469 A1* | 8/2004 | Tremont | 433/68 |
| 2006/0003285 A1* | 1/2006 | Kotsuchibashi et al. | 433/68 |
| 2006/0247517 A1 | 11/2006 | Labadie et al. | |
| 2006/0281991 A1* | 12/2006 | Fitzpatrick et al. | 600/426 |

FOREIGN PATENT DOCUMENTS

| | | |
|---|---|---|
| FR | 2831795 | 5/2003 |
| JP | 2005-52304 | 3/2005 |
| WO | 03/028574 | 4/2003 |

OTHER PUBLICATIONS

Medtronic Sofamor Danec Co., Ltd., "Ear, Nose, and Throat: products and therapies", 2008, www.medtronic.com/for-healthcare-professionals/products-therapies/ear-nose-throat/, 3 pages.
International Search Report corresponding to International Application No. PCT/JP2009/065802 filed Sep. 10, 2009.

* cited by examiner

*Primary Examiner* — Patricia Bianco
*Assistant Examiner* — Tarla Patel
(74) *Attorney, Agent, or Firm* — Squire Sanders (US) LLP

(57) ABSTRACT

An antenna holder for navigation surgery is provided to be used for a navigation surgery to a subject portion including a temporal bone region and a lateral skull base region of a patient. The antenna holder for navigation surgery comprises a mouth gag (an antenna holder) which is attached to a mouth of the patient and maintains the mouth of the patient opened, and an attachment arm which holds an antenna used for measuring a specific position of the subject portion.

4 Claims, 8 Drawing Sheets

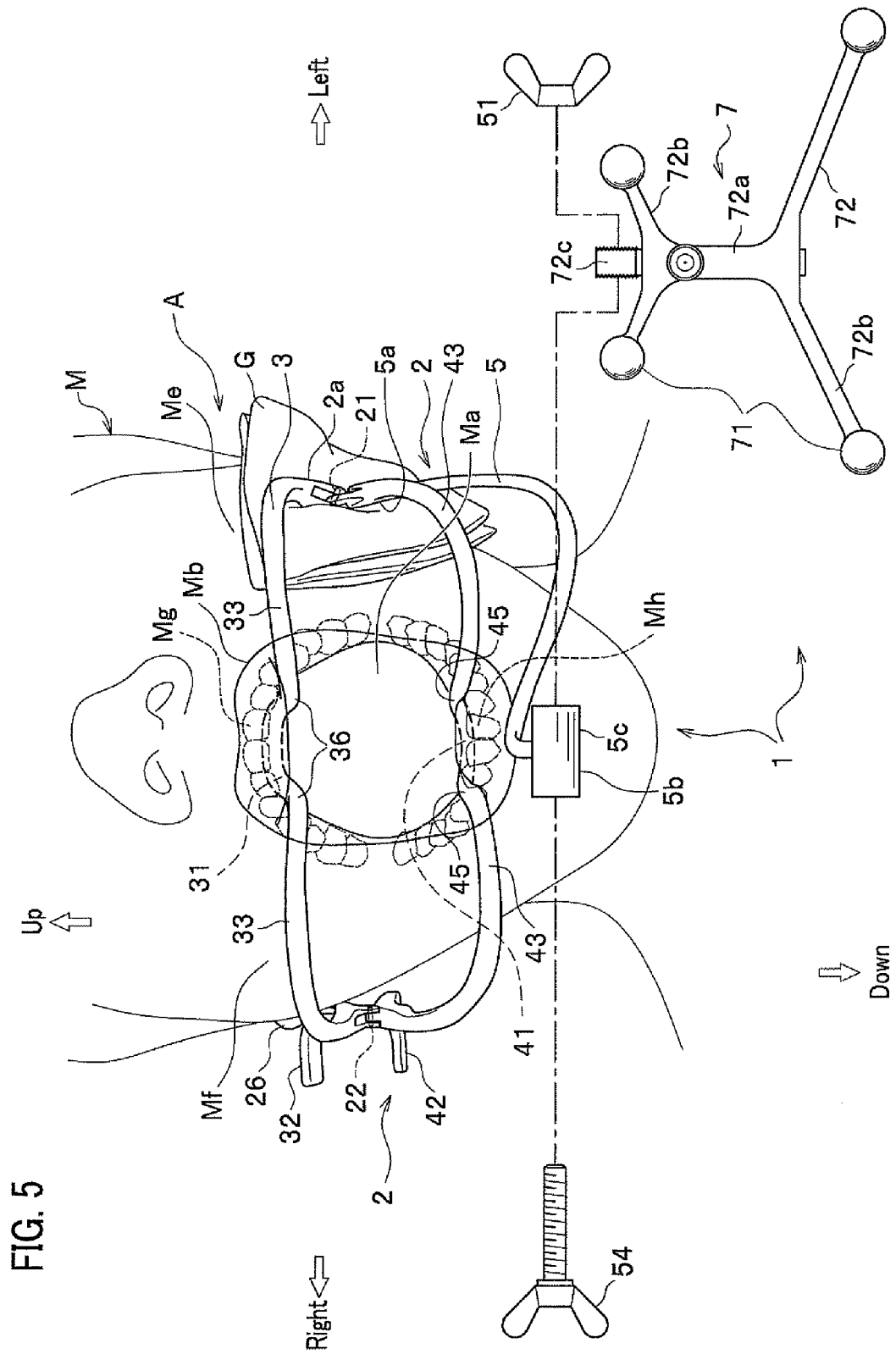

ANTENNA HOLDER FOR NAVIGATION SURGERY

TECHNICAL FIELD

The present invention relates to an antenna holder for navigation surgery used in a surgery navigation system (or surgery supporting system) which supports a physician to monitor an operational direction of the surgery. The system displays a position of a leading end of a position detecting instrument on the imaging data of CT, MRI and so forth shown by a display.

BACKGROUND ART

Recently, from the standpoint of surgical safety, etc., demands for widely using a navigation surgery in the field of neurosurgery have grown for the temporal bone region and the lateral skull base region. According to such surgical navigation system, a tomographic image by CT or MRI set forth captured beforehand is synthesized by a computer to display a tomogram or three-dimensional image on a display. Further, a shape of a surgical instrument or the like used for a surgery is registered beforehand, and a position of a marker attached to such a surgical instrument is detected by infrared or the like, thereby displaying the position of the leading end of the surgical instrument in use on the imaging data. Also, a holder for an antenna with a reference marker for detecting a position is attached to a patient. The position of the patient is calculated and aligned with the detected position of the surgical instrument, and those positions are displayed as an image by the surgery navigation system (or surgery supporting system). This system enables a surgeon to operate while figuring out a precise position inside an internal structure and recognizing the shape thereof during the surgery.

FIG. 8 is a perspective view showing how a position detection antenna used in a conventional surgical navigation system for a paranasal sinus surgery is attached.

As shown in FIG. 8, according to a conventional surgical navigation system 100, it is necessary to attach an antenna 200 for measuring a specific position of a subject portion of a patient at a position of the patient that synchronously moves as the subject portion of the patient moves. The antenna 200 shown in FIG. 8 and used for a paranasal sinus surgery is fixed to the head of the patient by an antenna holder for navigation surgery 300 including suction pads 310 that stick to the forehead of the patient, and a band 320 wrapped around the head (see, for example, Non-patent Literature).

Further, an antenna for navigation surgery used in a neurosurgery operation is fixed by attaching an antenna holder for navigation surgery that holds the antenna to a retainer fixed to the head of a patient by inserting a screw member into the head (see, for example, Patent Literature 1).

FIG. 9 is a perspective view showing how a position detection antenna used in a conventional surgical navigation system for surgeries of the temporal bone region and the lateral skull base region is attached.

An antenna 500 for the conventional surgical navigation system used for a surgery of the temporal bone region and the lateral skull base region and shown in FIG. 9 is fixed to the head of a patient by inserting four screw members 510 provided together with the antenna 500 into the skull bone of the patient (for example, see Patent Literature 2).

PRIOR ART DOCUMENTS

Patent Literatures

Patent Literature 1: U.S. Pat. No. 6,236,875
Patent Literature 2: US2002/0038126A Non-Patent Literature Non-patent Literature: Medtronic Sofamor Danek Co., Ltd., Otorhinolaryngology, [online], [searched on Sep. 9, 2008], Internet <URL:http://www.sofamordanek.co.jp/medical/goods/surgical/html>

DISCLOSURE OF INVENTION

Problem to be Solved by the Invention

According to the antenna 500 and the retainer used in the surgical navigation system (not shown) for the temporal bone region and the lateral skull base region and shown in FIG. 9 and Patent Literature 2, however, apertures are opened in the skull bone of a patient, and the screw members 510 are inserted into the apertures, which results in giving a significant invasiveness and load on the patient. Accordingly, even though the surgical technology through the surgical navigation system is improved, patients are likely to try to avoid such a technology because of the invasiveness of the antenna 500 attached to a patient and of the attachment of the retainer thereof. This makes it difficult to apply the surgical navigation system to the surgery for the temporal bone region and the lateral skull bone region.

Hereby, patients to be subjected to a navigation surgery strongly prefer to have an antenna holder for navigation surgery which does not put a load and invasiveness on the patient, thereby to be safely attached to a human body.

On the other hand, from the standpoint of surgeon, according to the conventional surgical navigation systems, it is necessary to carry out a surgical operation of opening apertures in specific locations of the bone of a patient, and to fix the screw members 510 into the apertures in order to fix the antenna 500 and the retainer to the body of the patient. Hence, attachment/detachment operations of the antenna 500 need extensive work.

Further, as can be seen from configuration shown in FIG. 9, it is difficult to sufficiently support the antenna 500, and thus the antenna becomes shaky and can be easily detached from the patient during a surgery. Accordingly, there is a demand from the surgeons for an antenna holder for navigation surgery which has little invasiveness to a patient subjected to a navigation surgery, is stable, and can be easily removed after surgery.

Further, when the antenna holder for navigation surgery 300 for a paranasal sinus surgery as shown in FIG. 8 is used for navigation surgeries of the temporal bone region and the lateral skull base region, at the time of the surgery, the head of a patient is rotated in the lateral direction to operate. Accordingly, the stability of the holder 300 is poor, and the band 320 of the holder 300 interferes with the surgical field and disturbs the surgery.

Hence, although the antenna holder for navigation surgery 300 for a paranasal sinus surgery has little invasiveness to a patient, it cannot be used for navigation surgeries of the temporal bone region and the lateral skull base region.

Furthermore, a surgical navigation system may be surgery assisting apparatus that can serve as a substitute for a senior supervising physician. Hence, in order to assist physicians having a few experiences and actual achievements to perform surgery safely and precisely, it is strongly desired to facilitate the surgical navigation system to be used widely.

Furthermore, in addition to being a surgical assistance as a substitute for a senior supervising physician, the surgical navigation system enables remote medical care such that an expert physician present at a remote location can advise a physician having a few actual achievements and present in an actual surgery room at an underpopulated area, etc., to perform surgery while watching a display and checking how the surgery advances. Accordingly, it is also strongly desired to facilitate the surgical navigation system to be used widely from such a standpoint.

The present invention has been made in order to overcome the foregoing problems. It is an object of the present invention to provide an antenna holder for navigation surgery which requires no surgical operation by a surgeon in attaching to the body of a patient, can be easily and firmly fixed but can be easily detached. Further, the antenna holder for navigation surgery should be attached with ease without a load and invasiveness to the patient subjected to a navigation surgery. Accordingly, the present invention provides an antenna holder for navigation surgery contributing to facilitate a surgical navigation system to be widely used for surgeries of the temporal bone region and the lateral skull base region.

Means for Solving the Problem

In order to accomplish the above object, a first aspect of the present invention provides an antenna holder for navigation surgery that is used for a navigation surgery to a subject portion including the temporal bone region and the lateral skull base region of a patient. Herein, the antenna holder for navigation surgery comprises: an antenna holder which is attached to the mouth of a patient and keeps the mouth of the patient opened; and an attachment arm which is attached to the antenna holder and holds an antenna used for measuring a specific position of the subject portion.

Here, the antenna holder includes: an upper frame which has an upper-jaw support member formed at a center, and is arranged around the peripheries of right and left cheeks the upper-jaw support member being supported at a mouth-cavity side of upper-jaw front teeth of the patient; and a lower frame that includes a lower-jaw support member supported at a mouth-cavity side of a lower-jaw front teeth of the patient. The upper frame and the lower frame have a first axial support which is arranged at respective one ends of the upper frame and the lower frame and rotatably couples the upper frame and the lower frame. Further, the upper frame and the lower frame have a second axial support which is arranged at respective another ends of the upper frame and the lower frame and rotatably couples the upper frame and the lower frame. Furthermore, grips are formed at respective leading ends beyond the second axial support.

According to such a configuration, the antenna holder for navigation surgery can allow the antenna holder to which the antenna is attached to maintain the mouth of the patient opened and to be fixed to the mouth of the patient, thereby allowing the antenna to be easily and firmly fixed to the patient. The antenna holder requires no surgical operation, and can be easily attached to and detached from the mouth of a patient without damaging a human body, so that a problem of invasiveness which occurs when the antenna holder for navigation surgery is attached to the body of a patient can be eliminated. Accordingly, the patient can have a navigation surgery without any mental load.

The antenna holder for navigation surgery makes an attachment work by screw-in to a bone through a surgical operation unnecessary, can be easily attached to the body of the patient, and is stably fixed. This may contribute to facilitate a navigation surgery to be used for the temporal bone region and the lateral skull base region including a middle ear, internal ear, etc., which was not popular conventionally.

A second aspect of the present invention provides the antenna holder for navigation surgery of the first aspect of the present invention in which the antenna is attached to an end opposite to the grips of the antenna holder.

According to such a configuration, when attached to the mouth of the patient, the antenna holder for navigation surgery allows the upper-jaw support member of the upper frame and the lower-jaw support member of the lower frame of the antenna holder to be inserted in the mouth cavity, and to be engaged with respective mouth-cavity sides of the upper-jaw front teeth and the lower-jaw front teeth, thereby being easily and surely fixed. Accordingly, the antenna holder for navigation surgery can simplify an attachment operation to the human body and reduce the time needed for the attachment, with a sure fixation.

A third aspect of the present invention provides the antenna holder for navigation surgery of the second aspect of the present invention in which the antenna is coupled to an end of the upper frame or the lower frame, the end being located at a side of the patient subjected to a surgery.

According to such a configuration, at the time of a navigation surgery, the antenna is coupled to the end of the upper frame or the lower frame at the side of the patient subjected to a surgery, which facilitates the antenna to be always directed to a position measuring device (an infrared sensor). Further, when a surgeon performs a surgery, the antenna holder for navigation surgery can be arranged so as not to bother the surgeon. This results in a contribution to facilitate a navigation surgery to be used for the temporal bone region.

A fourth aspect of the present invention provides the antenna holder for navigation surgery of the third aspect of the present invention in which the attachment arm is positioned so that the antenna is located at a weighted center of the antenna holder for navigation surgery.

According to such a configuration, because the attachment arm is positioned so that the antenna is located at the weighted center of the antenna holder for navigation surgery, the antenna holder can be stably fixed to the mouth of the patient without a wobble.

Effect of the Invention

According to the present invention, there is provided an antenna holder for navigation surgery which needs no surgical operation by a surgeon when attached to a body of a patient, can be easily and firmly fixed but can be easily detached, and can be attached with ease without a load and invasiveness to the patient subjected to a navigation surgery. Thereby, this may contribute to facilitate a surgical navigation system for surgeries of the temporal bone region and the lateral skull base region.

BRIEF DESCRIPTION OF THE DRAWINGS

FIG. 5 is an exploded perspective view showing the antenna holder for navigation surgery according to the embodiment of the present invention;

DETAILED DESCRIPTION OF THE PREFERRED EMBODIMENT

An explanation will be given for, prior to explaining an antenna holder for navigation surgery 1 of the present invention, the temporal bone region A where a navigation surgery is performed by using the antenna holder for navigation surgery 1 and a surgical navigation system 10 with reference to FIGS. 1A, 1B and 2. An explanation will be given for an illustrative embodiment of the present invention in which the left temporal bone region A is subjected to a surgery by the surgical navigation system 10.

The antenna holder for navigation surgery 1 of the present invention can be used not only for the temporal bone region A of a patient M but also for a case in which a surgery is performed on the lateral skull base region located at an occipital area relative to the temporal bone region A. In order to simplify the explanation, it is presumed that the top of the head of the patient M where the antenna holder for navigation surgery 1 is attached is the upper side and the lower limb of the patient M is the lower side.

<<Explanation for Temporal Bone Region>>

Figure 1A:
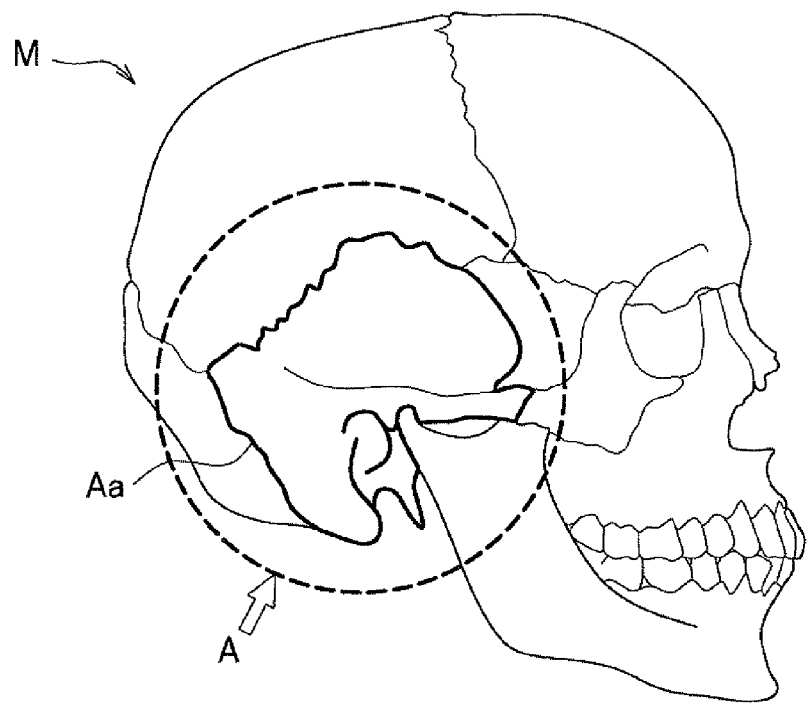
FIG. 1A is a diagram showing the location of the temporal bone region, and is a side view of the bone of a head.
Figure 1B:
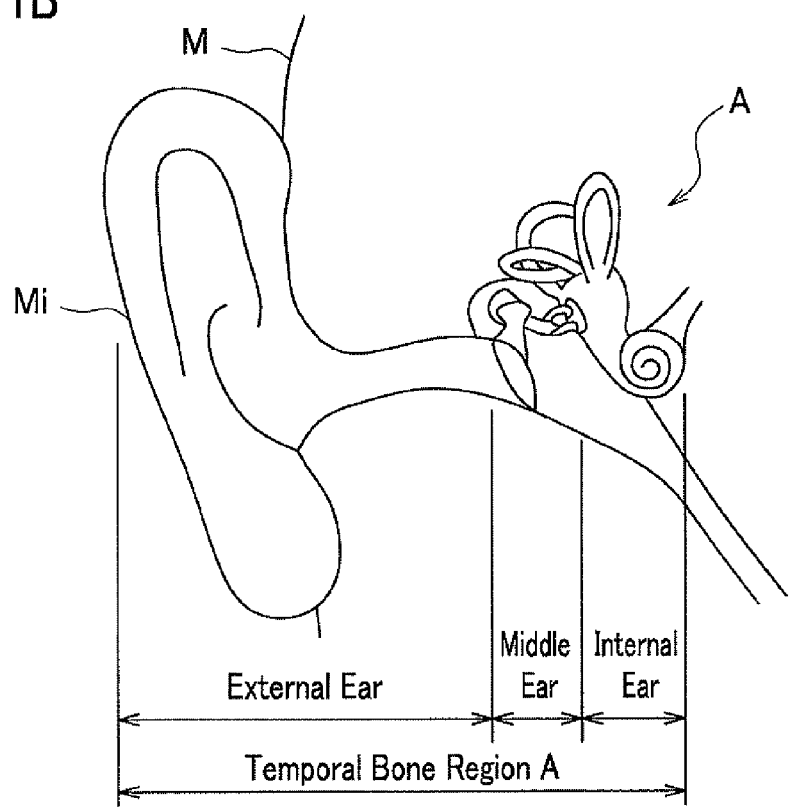
FIG. 1B is a diagram showing the location of the temporal bone region, and is an explanatory diagram for the internal structure of an ear.
Figure 2:
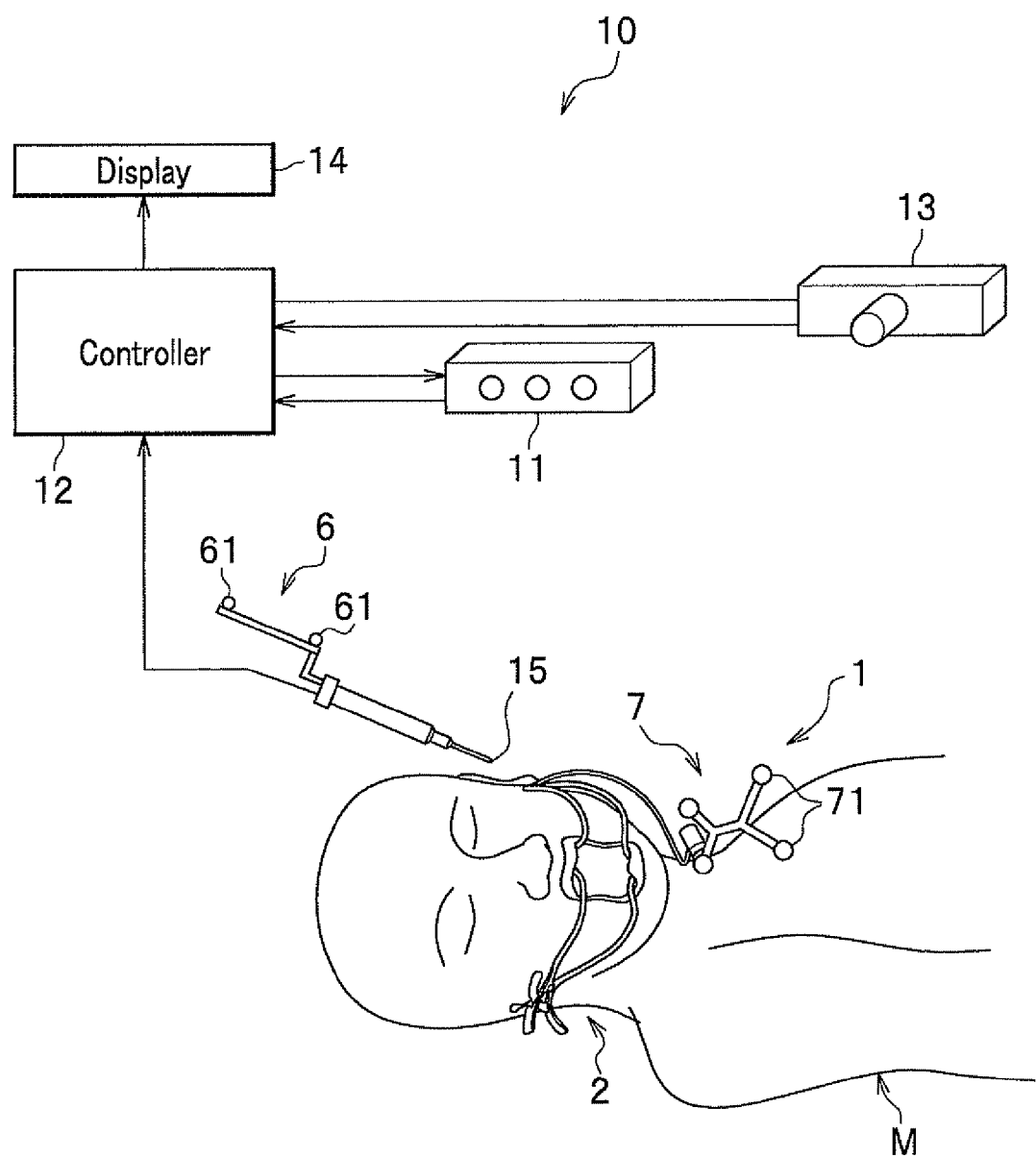
FIG. 2 is a block diagram showing a surgical navigation system using an antenna holder for navigation surgery according to an embodiment of the present invention.

As shown in FIG. 1A, the temporal bone region A is a subject portion to a navigation surgery by the surgical navigation system 10 (see FIG. 2). The temporal bone region A is a periphery of the temporal bone Aa including the temporal bone Aa, and as shown in FIG. 1B, includes the external ear, the middle ear, the internal ear, nerves represented by the facial nerve, and major vascular tissues (sinus venosus, cervical vein, and internal cervical vein).

<<Configuration of Surgical Navigation System>>

As shown in FIG. 2, the surgical navigation system 10 performs calculation on a tomographic image taken beforehand by, for example, a CT or an MRI in order to display an image in a tomographic or three-dimensional manner on a display 14. Further, the surgical navigation system 10 registers the position of the leading end of a position measuring instrument 15 (e.g., a probe) used for a surgery beforehand, attaches a position detection marker 61 to the position measuring instrument 15, and determines a position by, for example, infrared from a position measuring device 11. Accordingly, the surgical navigation system 10 displays the position of the leading end of the position measuring instrument 15 in use on imaging data, calculates positional coordinates of the patient M detected by attaching an antenna 7 with a patient marker 71 for position detection to the patient M, and simultaneously displays the calculated position on the tomographic image.

This allows the surgical navigation system 10 to display in a real-time manner, where the position of the leading end of the position measuring instrument 15 is located compared to the position of the image of the subject portion of the patient M taken prior to or during a surgery, thereby to provide an image guide. Further, the surgical navigation system 10 enables a surgeon to recognize an important but invisible tissue located deeply inside the body of the patient, to assist the surgeon.

The surgical navigation system 10 includes the position measuring device 11, a controller 12, a surgical microscope 13, the display 14, the position measuring instrument 15, a position measuring antenna 6, and the antenna holder for navigation surgery 1, all of which are discussed in detail later.

<<Configuration of Position Measuring Device>>

The position measuring device 11 detects respective positions of the patient marker 71 of the antenna 7 and the position detection marker 61 of the position measuring antenna 6. The position measuring device 11 includes, for example, an emitting unit which emits an infrared ray, and a receiving unit which receives the infrared ray emitted by the emitting unit, reflected by the patient marker 71 and returned. The position measuring device 11 has an infrared sensor compatible with the type of the patient marker 71 and that of the position detection marker 61, thereby to detect respective positions (or directions).

<<Configuration of Controller>>

As shown in FIG. 2, the controller 12 is a computer which calculates where the position measuring instrument 15 is located based on the infrared reflected by the position detection marker 61 of the position measuring instrument 15 and the infrared reflected by the patient marker 71 on the antenna holder for navigation surgery 1 attached to the patient M. The controller 12 controls the display 14 or the like so as to display the calculated position in a CT or MRI image taken and captured beforehand. The controller 12 includes, for example, a display control unit, a memory unit, an image generating unit, and a coordinate integrating process unit.

<<Configuration of Surgical Microscope>>

The surgical microscope 13 is a device which allows the surgeon to observe the subject portion (the temporal bone region A) of the patient M in a preferably enlarged manner to perform the surgery. The surgical microscope 13 has a mirror movable in all directions by an arm support mechanism, and is arranged at the surgery side (left side) of the patient M on a surgery bed B (see FIG. 6) in a surgery room.

<<Configuration of Display>>

As shown in FIG. 2, the display 14 is a device that displays various data, such as imaging data taken beforehand and stored in the memory unit (not shown) of the controller 12, and imaging data on the subject portion by the surgical microscope 13. The display 14 comprises, for example, a liquid crystal display or a CRT.

<<Configuration of Position Measuring Instrument>>

The position measuring instrument 15 is, for example, a needle, a clamp, or a drill used when surgery is performed on the temporal bone region A of the patient M. The position detection antenna 6 including the position detection marker 61 is attached to the position measuring instrument 15. The position of the position measuring instrument 15 to which the position detection marker 61 is attached is detected by infrared or the like from the outside. Accordingly, the position of the leading end of the position measuring instrument 15 registered on the imaging data beforehand is displayed on the patient imaging data on the display 14.

<<Configuration of Antenna Holder for Navigation Surgery>>

Figure 3:
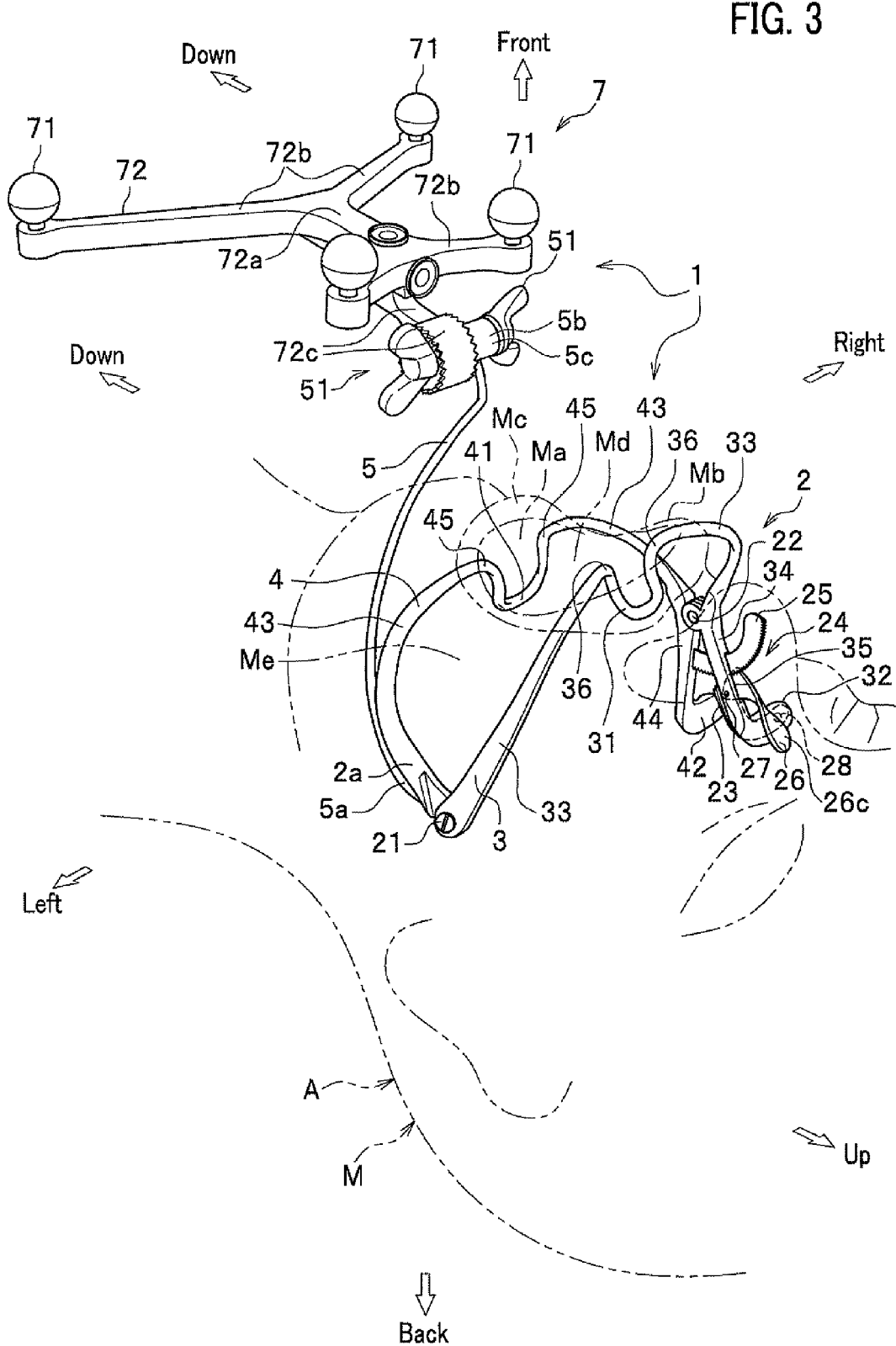
FIG. 3 is a perspective view showing the antenna holder for navigation surgery according to the embodiment of the present invention.

As shown in FIG. 3, the antenna holder for navigation surgery 1 has the antenna 7 fixed to a mouth cavity Md of the patient M, allowing the position of the subject portion to be detected by the position measuring device 11 (see FIG. 2) to enable tracking. The antenna holder for navigation surgery 1 mainly includes a mouth gag 2 which is fixed to the mouth cavity Md of the patient M and serves as an antenna holder, and the antenna 7 fixed to the mouth gag 2. The antenna holder for navigation surgery 1 can display an image of a precise position of the subject portion of the patient M by attaching the antenna holder for navigation surgery 1 to the patient M.

<<Configuration of Mouth Gag (Antenna Holder)>>

As shown in FIG. 3, the mouth gag 2 is an apparatus that keeps a mouth Ma of the patient M to be opened. The mouth gag 2 is an improved type of Jennings mouth gag commercially available as an apparatus that maintains the mouth Ma to be opened at the time of, for example, a surgery to a tongue. Herein, the mouth gag 2 has grips 32, 42 formed in a short length and has the antenna 7 attached through an attachment arm 5 and fasteners 51. The mouth gag 2 includes an upper frame 3, a lower frame 4, a first axial support 21, a second axial support 22, a spring member 23, a ratchet mechanism 24, a ratchet gear-teeth piece 25, a lock release lever 26, and an axial support pin 27, all of which are discussed in detail later.

The mouth gag 2 causes the upper frame 3 and the lower frame 4 which are curved along right and left cheeks Me, Mf (see FIG. 5) with the mouth Ma of the patient M being as a substantial center to rotate around the first axial support 21 arranged at the left of the mouth gag 2 and the second axial support 22 arranged at the right of the mouth gag 2 by rotating and operating the grips 32, 42, thereby causing an upper-jaw support member 31 and a lower-jaw support member 41 to be spaced apart or to come close together (see FIGS. 4 and 5). The mouth gag 2 is formed of, for example, a bent bar-like metal which does not easily erode like stainless steel. Note that the mouth gag 2 corresponds to an "antenna holder" in claims.

<<Configuration of Upper Frame>>

As shown in FIG. 3, the upper frame 3 is a bar-like member which maintains the upper-jaw side of the mouth Ma of the patient M to be opened, and is rotatable up and down around the first axial support 21 at the left end and the second axial support 22 at the right end. The upper frame 3 includes the first axial support 21, the second axial support 22, the upper-jaw support member 31, curved portions 33, 33, a leg 34, an elongated opening 35, the grip 32, the spring member 23, the lock release lever 26, the axial support pin 27, and a spring fixing member 28, all of which are discussed in detail later. The upper frame 3 is arranged at the outer circumferences of the right and left cheeks Me, Mf (see FIG. 5) with the upper-jaw support member 31 which is inserted in the mouth cavity Md through an upper lip Mb of the patient M and which is supported at the mouth-cavity-Md side of upper-jaw front teeth Mg (see FIG. 5) being as a substantial center. The upper frame 3 has a right part formed longer than the left part by what corresponds to the leg 34 and the grip 32.

<<Configuration of Lower Frame>>

The lower frame 4 is a bar-like member which maintains the lower-jaw side of the mouth Ma of the patient M to be opened, and is rotatable up and down around the first axial support 21 at the left end and the second axial support 22 at the right end. The lower frame 4 includes the first axial support 21, the second axial support 22, the lower-jaw support member 41, curved portions 43, 43, a leg 44, and the grip 42, all of which are discussed in detail later. The lower frame 4 is arranged at the outer circumferences of the right and left cheeks Me, Mf (see FIG. 5) with the lower-jaw support member 41 which is inserted in the mouth cavity Md through a lower lip Mc of the patient M and which is supported at the mouth-cavity-Md side of lower-jaw front teeth Mh (see FIG. 5) being as a substantial center. The upper frame 3 and the lower frame 4 have respective grips 32, 42, formed at respective leading-end sides over the second axial support 22. When the surgeon rotates and operates the grips 32, 42, the upper frame and the lower frame are opened/closed in a substantially symmetrical shape around the first axial support 21 and the second axial support 22.

<Configurations of First Axial Support and Second Axial Support>

The first axial support 21 is a pin which joins the left end of the upper frame 3 and the left end of the lower frame 4 together in a rotatable manner up and down, supports those frames, and is arranged at respective left ends of the upper frame 3 and the lower frame 4.

The second axial support 22 is a pin which joins the right end of the upper frame 3 and the right end of the lower frame 4 together in a rotatable manner up and down, supports those frames, and is arranged at respective right ends of the upper frame 3 and the lower frame 4.

<Configuration of Upper-Jaw Support Member>

As shown in FIG. 3, the upper-jaw support member 31 is supported (see FIG. 5) by, when the upper-jaw support member 31 is inserted in the mouth cavity Md in order to attach the mouth gag 2 to the patient M, being pushed against the mouth-cavity-Md side of the upper-jaw front teeth Mg (see FIG. 5) and by pushing widely the upper dental arch upwardly by transition portions 36 between the upper-jaw support member 31 and respective curved portions 33. The upper-jaw support member 31 is formed by bending the center part of the upper frame 3 between the first axial support 21 and the second axial support 22 in a substantially rectangular shape with one side being opened in a planar view (see FIG. 6), and is formed and directed to an oblique upper direction in a side view (see FIGS. 4A and 4B).

<Configuration of Lower-Jaw Support Member>

As shown in FIG. 3, the lower-jaw support member 41 is supported by, when the lower-jaw support member 41 is inserted in the mouth cavity Md in order to attach the mouth gag 2 to the patient M, being pushed against the mouth-cavity-Md side of the lower-jaw front teeth Mh (see FIG. 5) and by pushing widely the lower dental arch downwardly by transition portions 45 between the lower-jaw support member 41 and respective curved portions 43. The lower-jaw support member 41 is formed by bending the center part of the lower frame 4 between the first axial support 21 and the second axial support 22 in a substantially rectangular shape with one side being opened in a planar view, and is formed and directed to an oblique lower direction in a side view (see FIGS. 4A and 4B).

<Configurations of Curved Portions>

The curved portions 33, 33, 43, 43 of the upper frame 3 and the lower frame 4 are portions running from both right and left sides of the upper-jaw support member 31 and the lower-jaw support member 41 and curved along the cheeks Me, Mf (see FIG. 5) of the patient M toward the direction of the occipital area.

<Configurations of Legs>

The legs 34, 44 (see FIG. 4A) of the upper frame 3 and the lower frame 4 extend from respective right curved portions 33, 43 to the occipital-area side along the cheeks Me, Mf (see FIG. 5) of the patient M through the second axial support 22. The leg 34 of the upper frame 3 has, in the vertical direction, the elongated opening 35 where the ratchet gear-teeth piece 25 is inserted with a play and the lock release lever 26 is arranged in a rotatable manner. The leg 44 of the lower frame 4 is fixed with the basal end of the ratchet gear-teeth piece 25 inserted in the elongated opening 35 with a play by, for example, welding.

<Configurations of Grips>

As shown in FIG. 3, the grips 32, 42 are portions where fingers of the surgeon are placed when the distance between the center portion of the upper frame 3 and the center portion of the lower frame 4 of the mouth gag 2 is increased or decreased. The grips 32, 42 are formed in a substantially L shape bent from respective leading ends of the legs 34, 44.

Figure 6:
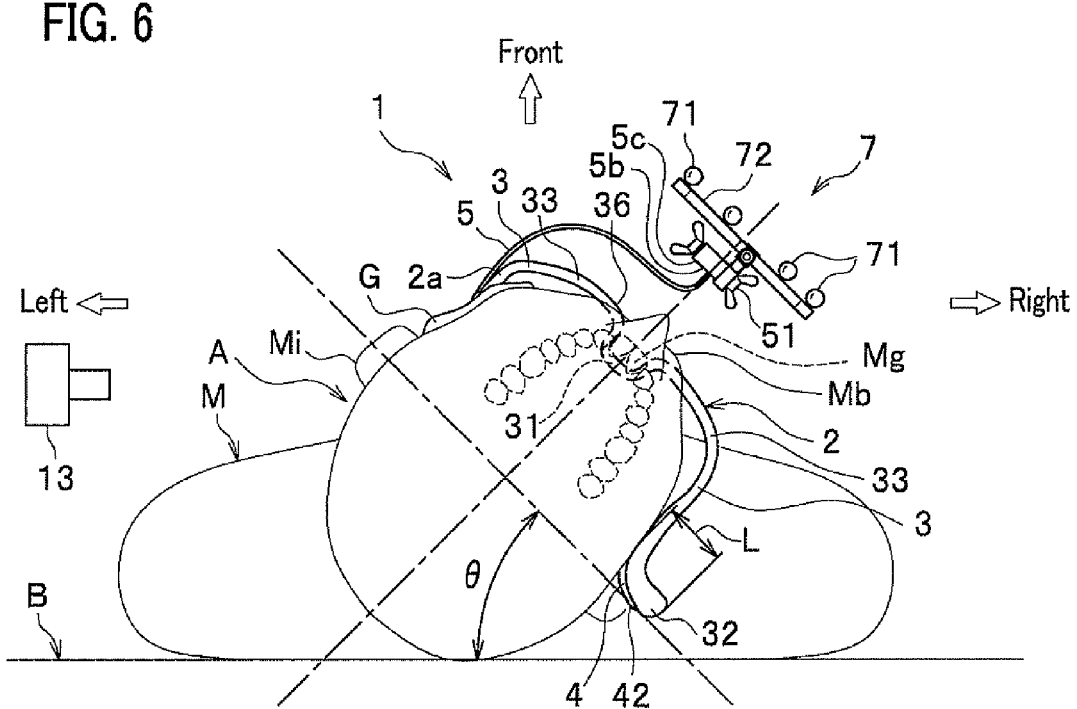
FIG. 6 is a plan view showing how the antenna holder for navigation surgery is arranged when a surgery to the temporal bone region is performed using the antenna holder for navigation surgery according to the embodiment of the present invention.

As shown in FIG. 6, when surgery is performed on the left temporal bone region A that is the subject portion, the patient M is placed on the surgery bed B with the head thereof being inclined so that the position of the left temporal bone region A is directed to the front direction (a direction toward a ceiling) inclined substantially 45 degrees. At this time, the grips 32, 42 are each formed to a length L that does not cause each leading end to contact the surgery bed B. The length L of each grip 32, 42 can be set to be, for example, a length from the leading end of a finger to the top joint thereof in consideration of easiness of gripping. By forming the grips 32, 42 having the length L that is short and protrudes from the leading ends of respective legs 34, 44 to the widthwise direction (the right-and-left direction), the grips 32, 42 enable setting of the position of the temporal bone region A to be not only 45 degrees but also an angle θ that facilitates a surgery.

<Configuration of Ratchet Mechanism>

Figure 4A:
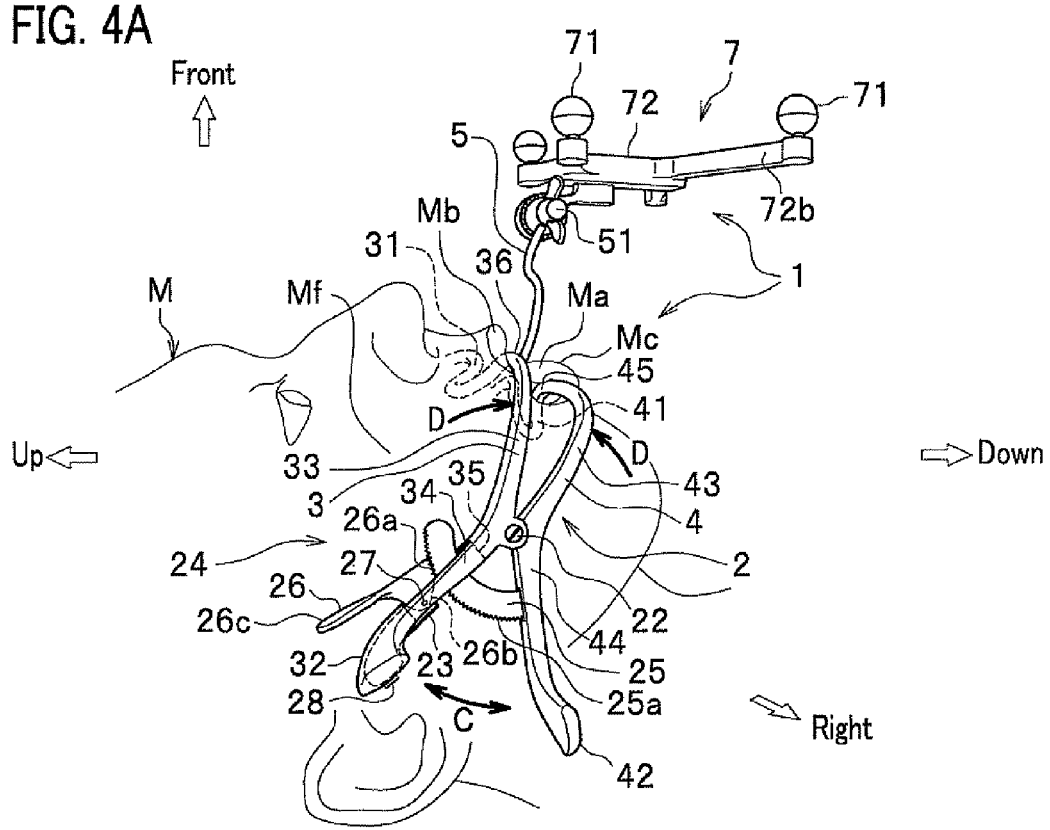
FIG. 4A is a diagram showing the antenna holder for navigation surgery according to the embodiment of the present invention, and is a side view showing how a mouth gag of the antenna holder for navigation surgery is set to the mouth of a patient.
Figure 4B:
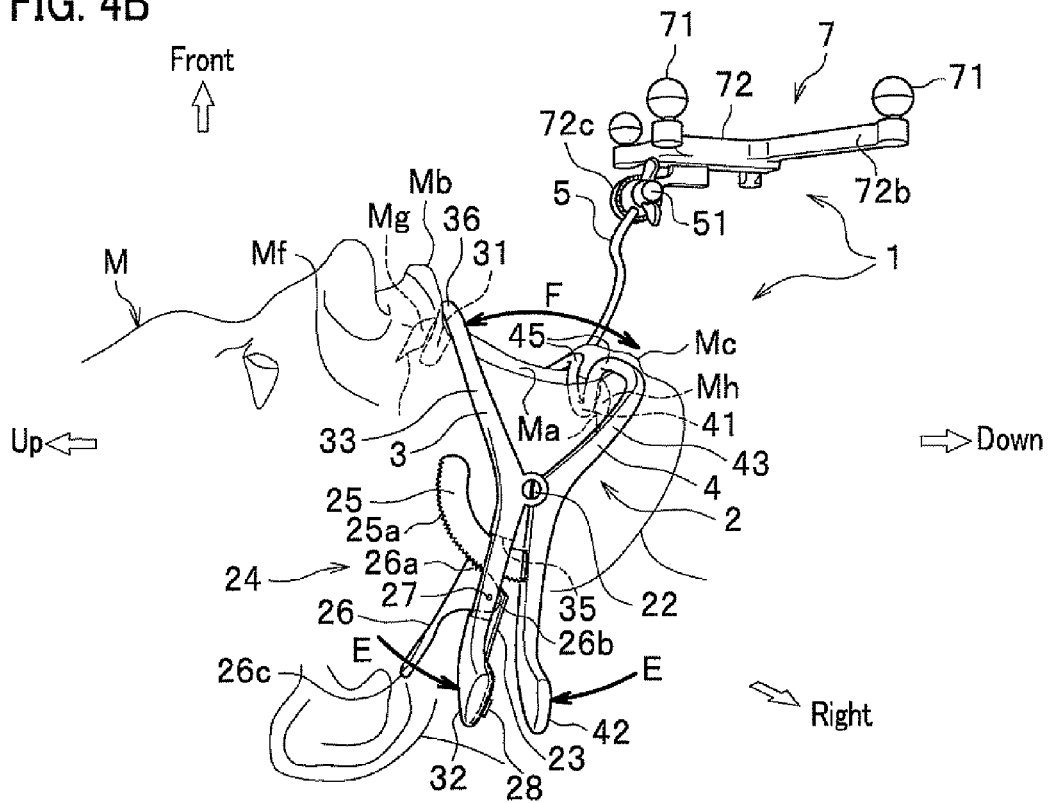
FIG. 4B is a diagram showing the antenna holder for navigation surgery according to the embodiment of the present invention, and is a side view showing how the mouth gag of the antenna holder for navigation surgery is fixed to a mouth maximum opened position with the mouth of the patient being opened largely.

As shown in FIGS. 4A, 4B, the ratchet mechanism 24 includes ratchet teeth 25a, and a stopper tooth 26a that meshes with the ratchet teeth 25a. The ratchet mechanism 24 turns only in a direction in which the upper frame 3 and the lower frame 4 become apart from each other when the grips 32, 42 are pinched by fingers and held in a gripping direction. By rotating and operating the lock release lever 26 so as to push it in, the stopper tooth 26a is moved apart from the ratchet teeth 25a, and the upper frame 3 and the lower frame 4 can be freely moved in an open direction or a closed direction.

<Configuration of Ratchet Gear-Teeth Piece>

The ratchet gear-teeth piece 25 is a belt-like tabular member formed in an arcuate shape around the second axial support 22 and provided with teeth formed around the outer circumference of the belt-like tabular member. The ratchet gear-teeth piece 25 has the basal end fixed to the leg 44 of the lower frame 4 by welding or the like.

<Configuration of Lock Release Lever>

The lock release lever 26 is a stopper which enables the upper frame 3 and the lower frame 4 that are rotatable around the first axial support 21 (see FIG. 3) and the second axial support 22 to be rotatable/unrotatable. The lock release lever 26 has the stopper tooth 26a, a push member 26b, and a pinch 26c. The lock release lever 26 is supported by an axial support pin 27 in a rotatable manner.

As shown in FIGS. 4A and 4B, the stopper tooth 26a is a stopper which meshes with the ratchet teeth 25a of the ratchet gear-teeth piece 25 and disables the upper frame 3 and the lower frame 4 to rotate. When, for example, the upper frame 3 is rotated and moved in a direction (a direction indicated by an arrow E) coming close to the grip 42 of the lower frame 4, the stopper tooth 26a turns around the periphery of the ratchet teeth 25a arranged in an arcuate manner with no engagement. This enables the distance between the upper-jaw support member 31 and the lower-jaw support member 41 to be increased.

In contrast, when the grip 32 of the upper frame 3 is rotated and moved in a direction (a direction indicated by an arrow C) becoming apart from the grip 42 of the lower frame 4, the stopper tooth 26a meshes with the ratchet teeth 25a, and the upper and lower frames become unrotatable unless the stopper tooth 26a is moved apart from the ratchet teeth 25a.

The push member 26b is elastically pushed by the spring member 23, thereby applying a biasing force against the lock release lever 26 to be rotated in a locking direction. The push member 26b is formed in a triangular shape in a side view.

The pinch 26c is a portion pinched by a finger when the lock release lever 26 is operated.

<Configuration of Axial Support Pin>

The axial support pin 27 is a pin to rotatably support the lock release lever 26 in a condition in which the push member 26b protrudes from the elongated opening 35 to the spring member 23 side. The axial support pin 27 is provided in a condition in which the lock release lever 26 is inserted in the elongated opening 35 of the leg 34.

<Configuration of Spring Member>

As shown in FIGS. 4A, 4B, the spring member 23 is a spring which pushes the push member 26b of the lock release lever 26, allowing the stopper tooth 26a of the lock release lever 26 to mesh with the ratchet teeth 25a of the ratchet gear-teeth piece 25 and to be pushed against the ratchet teeth. The spring member 23 comprises a leaf spring having a basal end fixed to the grip 32 of the upper frame 3 by a spring fixing member 28 that is a tiny screw, and having a leading end arranged at a position to push the stopper tooth 26a.

<Configuration of Antenna>

As shown in FIG. 3, the antenna 7 is a patient-position measuring antenna which is attached to the mouth gag 2 and used to measure a specific position of the subject portion of the patient M. The antenna 7 includes a plurality of patient markers 71 used to measure the position of the subject portion, an array 72 having the plurality of patient markers 71, and the attachment arm 5 for fixing the array 72 to the mouth gag 2. The antenna 7 is coupled to an end 2a of the mouth gag 2 at the side of the surgery-target part of the patient M. The antenna 7 is not limited to any particular one as long as it is a navigation-surgery antenna. The shape and the configuration thereof are not limited to any particular ones.

<Configurations of Patient Marker and Array>

The patient marker 71 is a spherical body that reflects infrared emitted from the emitting unit of the position measuring device 11 (see FIG. 2) to the receiving unit of the position measuring device 11.

The array 72 is a frame member having the four patient markers 71 attached to the leading ends of respective frame portions 72b each having a different length. The array 72 includes a main body 72a at the center, the frame portions 72b protruding in the right and left directions from both front and rear ends of the main body 72a, and a leg frame 72c protruding from the center of the main body 72a to the mouth gag 2 side. The array 72 is integrally formed by the above mentioned members.

<Configuration of Attachment Arm>

As shown in FIG. 6, the attachment arm 5 is arranged so that the array 72 is located at the weighted center of the antenna holder for navigation surgery 1. In other words, the attachment arm 5 is curved and extends toward the front of the face from the end 2a of the lower frame 4 located opposite to the positions of the grips 32, 42 so that the antenna 7 is located at the middle (the center) of the antenna holder for navigation surgery 1.

The attachment arm 5 has a cylindrical portion 5c which is welded to a leading end 5b and fixed to the array 72 in an appropriate direction by the fasteners 51. Further, the attachment arm 5 has a basal end 5a fixed to the end 2a of the lower frame 4 at the side of the surgery-target part (the temporal bone region A of a left ear Mi) of the patient M by welding or the like. For example, a screw part of a wing bolt to be engaged with a wing nut is inserted in the cylindrical portion 5c of the attachment arm 5, and is fixed by welding or the like with the cylindrical portion 5c being directed in the right-and-left direction.

The basal end 5a of the attachment arm 5 may be fixed to the end 2a of the upper frame 3 at the side of the surgery-target part of the patient M. The attachment arm 5 may have the leading end 5b side formed together with the antenna 7 and fixed, and the basal end 5a may be detachably attached to the mouth gag 2 in a non-movable manner. The fasteners 51 can be in any form in accordance with the shape of the antenna for navigation surgery.

<<Working of Antenna Holder for Navigation Surgery>>

Next, an explanation will be given of a working of the antenna holder for navigation surgery 1 according to the embodiment of the present invention.

When the antenna holder for navigation surgery 1 is fixed to the patient M, first, the patient M is placed on the surgery bed B (see FIG. 6), and is subjected to full anesthesia prior to a surgery, and then the mouth gag 2 is attached to the patient M.

In this case, as shown in FIG. 4A, the mouth gag 2 is operated in a direction in which the grips 32, 42 are moved apart (a direction indicated by an arrow C) while the lock release lever 26 being operated, rotated in a direction in which the upper-jaw support member 31 and the lower-jaw support member 41 come close (a direction indicated by the arrow D), and attached to the patient M. If the mouth gag 2 presses the cheeks Me, Mf of the patient M, a gauze G (see FIG. 5) is fitted to the pressed cheeks Me, Mf in order to protect the skin of the face, and fixing of the mouth gag 2 to the patient M is stabilized. Note that the gauze G is unnecessary if there is no pressing, and may be provided at not only one side but also both sides.

Next, the grips 32, 42 are located at the right cheek Mf, the mouth Ma of the patient M is opened, the upper-jaw support member 31 is applied to the mouth-cavity-Md side of the upper-jaw front teeth Mg, and the lower-jaw support member 41 is applied to the lower-jaw front teeth Mh, thereby setting the mouth gag 2 to the face of the patient M.

As shown in FIG. 4B, the mouth gag 2 is operated in a direction (a direction indicated by an arrow E) in which the grips 32, 42 come close to each other, fully rotated in a direction (a direction indicated by an arrow F) in which the upper-jaw support member 31 and the lower-jaw support member 41 are opened, and is firmly fixed to the facial part of the patient M at the mouth-maximum-open position.

As shown in FIG. 5, the mouth gag 2 attached in this fashion has the upper-jaw support member 31 engaged with the mouth-cavity-Md side of the upper-jaw front teeth Mg integral with the upper jaw bone of the patient M. The mouth gag 2 has the lower-jaw support member 41 engaged with the mouth-cavity-Md side of the lower-jaw front teeth Mh, so that the mouth gag is fixed to the mouth Ma with the mouth Ma being pushed and opened by the upper-jaw support member 31 and the lower-jaw support member 41. At this time, because the lower jaw movable relative to the upper jaw of the patient M in a fixed condition naturally moves in a direction in which the mouth Ma is closed, the mouth gag 2 is firmly and stably fixed in a condition in which the mouth gag becomes immovable, to be attached to the facial part of the patient M.

Because the antenna holder for navigation surgery 1 can be firmly fixed to the face of the patient M, when the head of the patient M moves, the antenna 7 also moves together with the subject portion. Therefore, the position of the subject portion can be measured and the coordinates of the subject portion of the head can be obtained, enabling the antenna 7 to be used for a navigation surgery to the temporal bone region A.

The antenna holder for navigation surgery 1 can be easily attached to the patient M with little invasiveness. When the upper-jaw support member 31 and the lower-jaw support member 41 are inserted in the mouth Ma of the patient M, the antenna holder for navigation surgery 1 can be attached to the facial part within a short time (around 30 seconds).

Accordingly, the antenna holder for navigation surgery 1 of the present invention does not need a conventional invasive fixing operation of screwing into the skull bone, which needs over 30 minutes. This can remarkably reduce the number of operation processes and the operation hours, which allows reducing the cost.

As shown in FIG. 6, the patient M to whom the antenna holder for navigation surgery 1 is attached is laid down in a condition in which the temporal bone region A at the left-ear-Mi side subjected to a surgery is directed towards the upward direction inclined about 45 degrees relative to the surgery bed B (see FIG. 6). During the surgery, the antenna holder for navigation surgery 1 has the antenna 7 located not in the vicinity of the temporal bone region A having undergone a navigation surgery, so that the antenna does not interfere with the surgical work.

The antenna holder for navigation surgery 1 fixed in this fashion to the patient M subjected to a navigation surgery has little load and invasiveness to the patient M without giving a pain to a tooth or a jaw after a surgery, and can be safely attached to a human body.

Modified Example

The present invention is not limited to the foregoing embodiment, and can be changed and modified in various forms within the scope and the spirit of the present invention, and those changed and modified forms are also included in the present invention.

Figure 7:
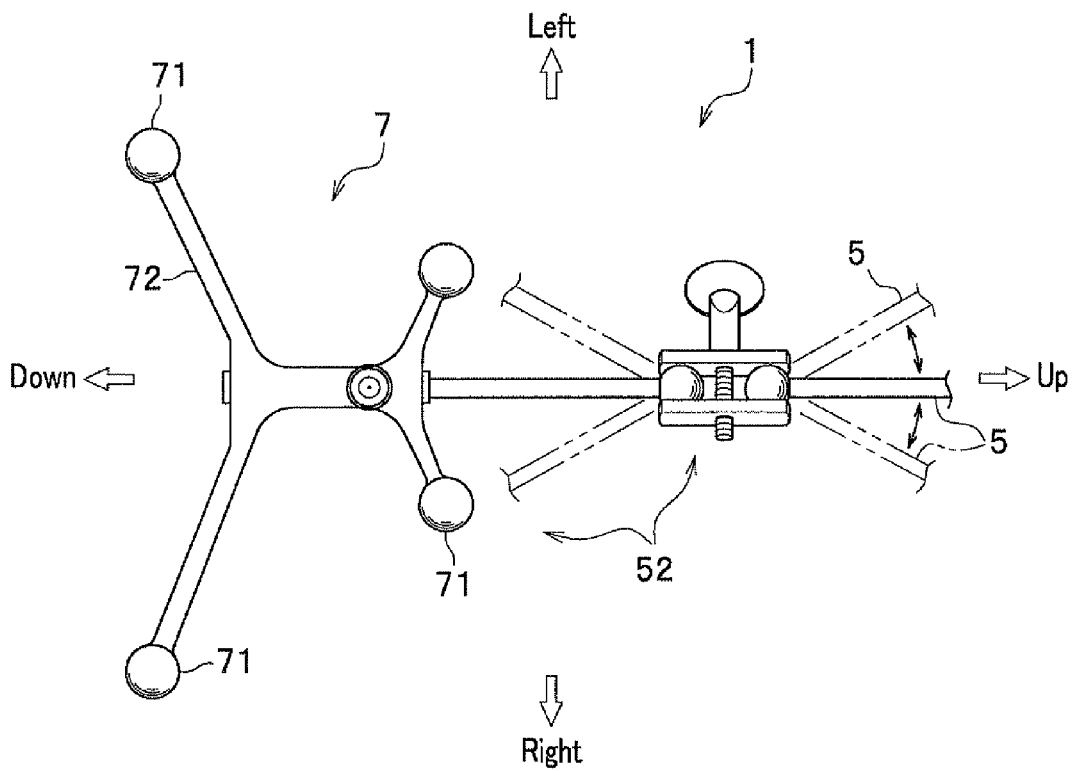
FIG. 7 is a perspective view showing a modified example of the antenna holder for navigation surgery according to an embodiment of the present invention.
Figure 8:
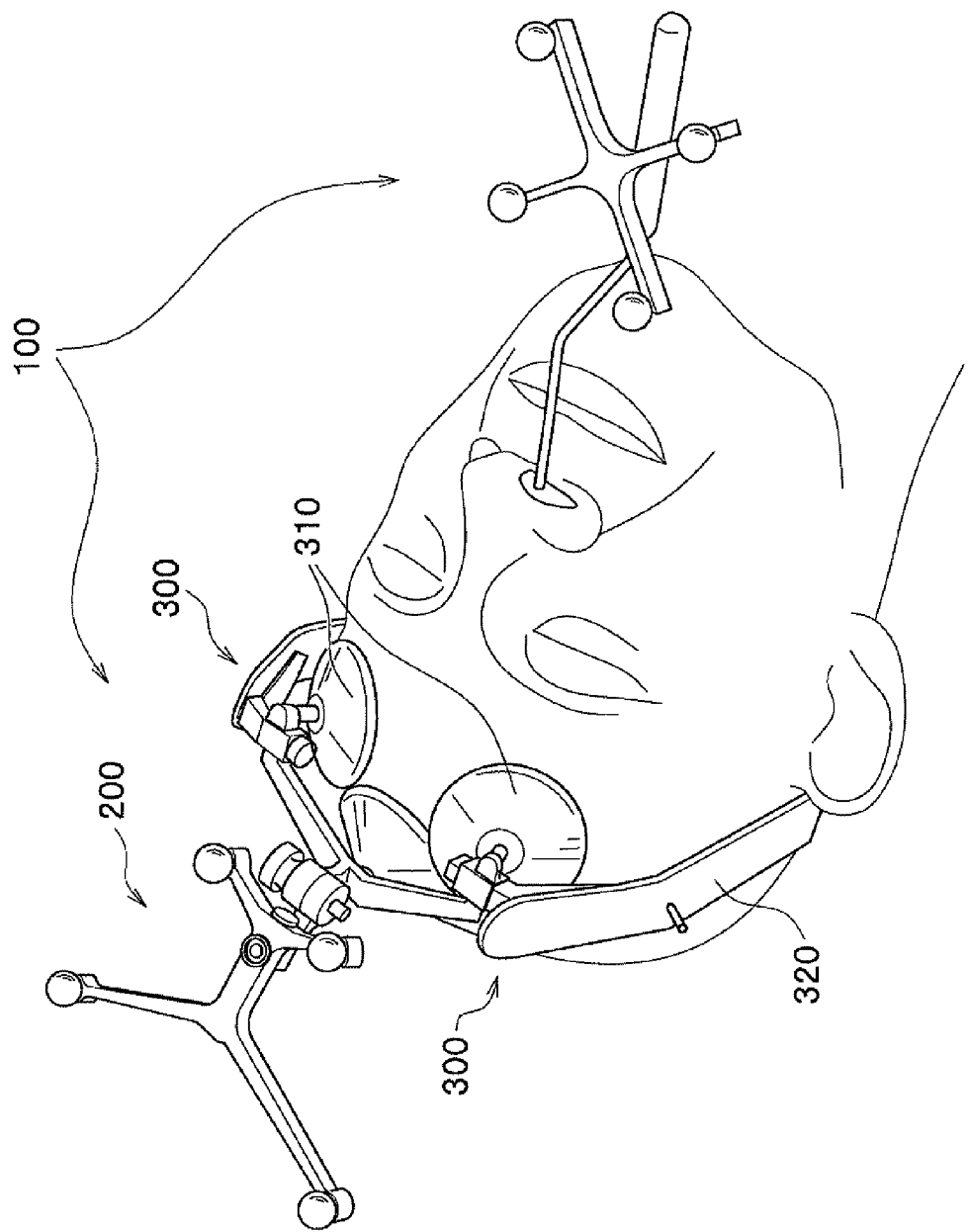
FIG. 8 is a perspective view showing how a position detection antenna used in a conventional surgical navigation system for a paranasal sinus surgery is attached.
Figure 9:
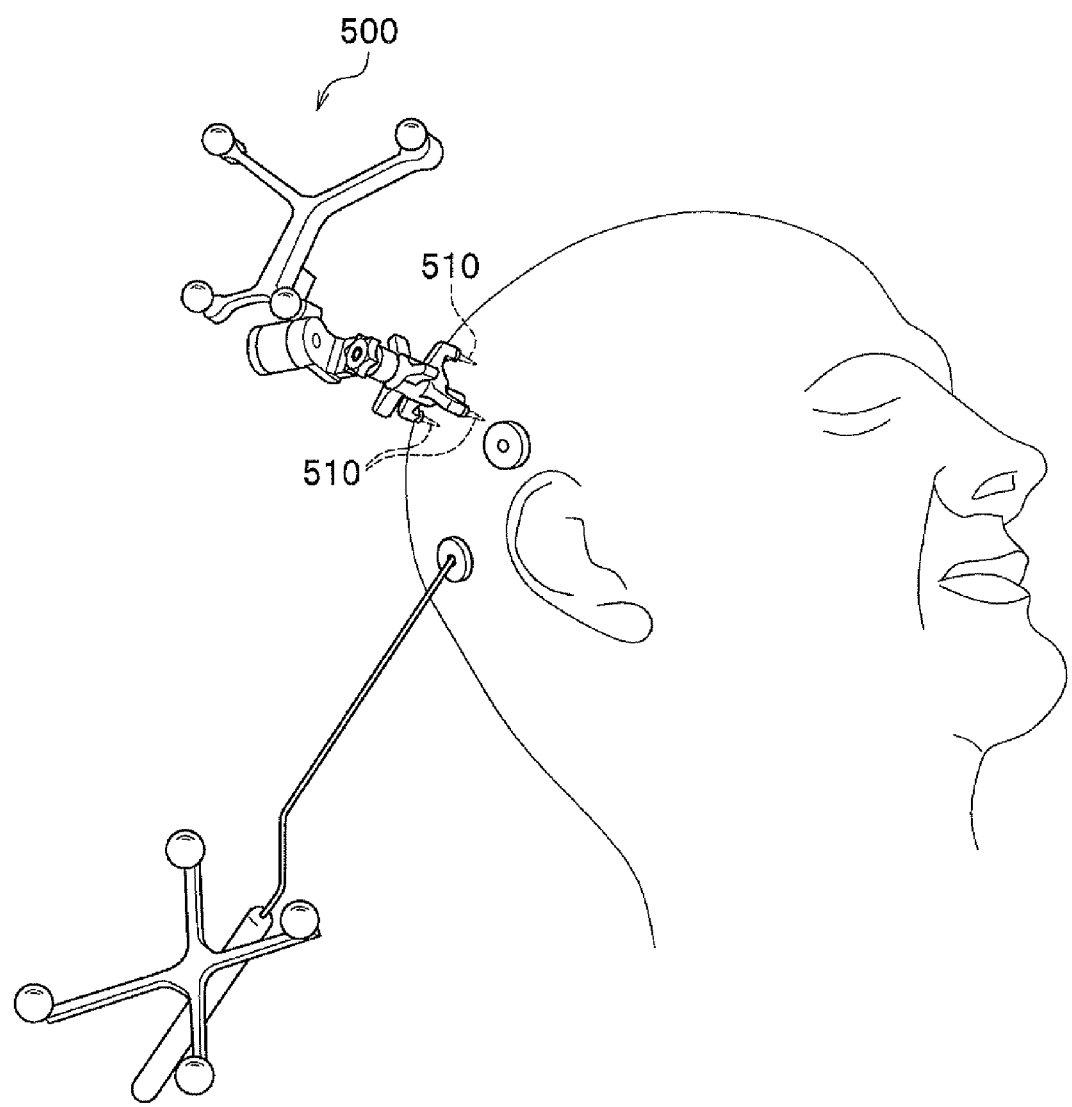
FIG. 9 is a perspective view showing how a position detection antenna used in a conventional surgical navigation system for surgeries of the temporal bone region and the lateral skull base region is attached.

FIG. 7 is a perspective view showing a modified example of an antenna holder for navigation surgery of the embodiment of the present invention.

In the foregoing embodiment, as shown in FIG. 5, the array 72 of the antenna 7 of the antenna holder for navigation surgery 1 is coupled to the attachment arm 5 through the fasteners 51. However, as shown in FIG. 7, a free joint 52 may be present between the array 72 and the attachment arm 5 in order to cause the antenna 7 to be movable in any direction.

This allows the antenna 7 to be located at a position where measurement by the position measuring device 11 becomes fine and a position where a surgeon is not interfered during the surgery.

In the foregoing embodiment, the explanation was given of an example case in which a surgery is performed on the left temporal bone region A, but the present invention can be applied to not only a case in which the opposite side is subjected to a surgery but also a case in which a surgery is performed on the lateral skull base region around the temporal bone region A. The present invention has a general versatility, and can be applied to a case in which a surgery is performed on head portions other than the foregoing regions.

The antenna holder for navigation surgery 1 may be formed of a non-magnetic body other than a metal like a hard resin which is not likely to be elastically deformed. This allows a navigation surgery using a CT or an MRI during the surgery.

DESCRIPTION OF REFERENCE NUMERALS

1 Antenna holder for navigation surgery
2 Mouth gag (antenna holder)
2a End
3 Upper frame
4 Lower frame
5 Attachment arm
7 Antenna
10 Surgical navigation system
21 First axial support
22 Second axial support
31 Upper-jaw support member
32, 42 Grips
36, 45 Transition portions
41 Lower-jaw support member
51 Fastener
71 Patient marker
72 Array
A Temporal bone region
M Patient
Ma Mouth
Mb Upper lip
Mc Lower lip
Md Mouth cavity
Me, Mf Cheeks
Mg Upper-jaw front teeth
Mh Lower-jaw front teeth

What is claimed is:

1. An antenna holder for navigation surgery that is used for a navigation surgery to a subject portion including a temporal bone region and a lateral skull base region of a patient, the antenna holder for navigation surgery comprising:
   an antenna holder which is attached to a mouth of the patient and maintains the mouth of the patient opened; and
   an attachment arm which is attached to the antenna holder and holds an antenna used for measuring a specific position of the subject portion, wherein
   the antenna holder includes:
   an upper frame which has an upper-jaw support member formed at a center, and is arranged around the peripheries of right and left cheeks, the upper-jaw support member being supported at a mouth-cavity side of upper-jaw front teeth of the patient; and
   a lower frame that includes a lower-jaw support member supported at a mouth-cavity side of a lower-jaw front teeth of the patient,
   the upper frame and the lower frame include a first axial support which is arranged at respective one ends of the upper frame and the lower frame and which rotatably couples the upper frame and the lower frame, a second axial support which is arranged at respective another ends of the upper frame and the lower frame and which rotatably couples the upper frame and the lower frame, and respective grips formed at respective leading ends beyond the second axial support.

2. The antenna holder for navigation surgery according to claim 1, wherein the antenna is attached to an end opposite to the grips of the antenna holder.

3. The antenna holder for navigation surgery according to claim 2, wherein the antenna is coupled to an end of the upper frame or the lower frame, the end being located at a side of the patient subjected to a surgery.

4. The antenna holder for navigation surgery according to claim 3, wherein the attachment arm is positioned so that the antenna is located at a weighted center of the antenna holder for navigation surgery.

* * * * *